United States Patent [19]

Swarthout et al.

[11]  4,204,983

[45]  May 27, 1980

[54] ABSORBENT POLYMERIC COMPOSITIONS DERIVED FROM AMYLACEOUS MATERIAL-FORMALDEHYDE SUBSTRATES

[75] Inventors: E. Jack Swarthout; Phillip Antholz, both of Paris, Ill.

[73] Assignee: Illinois Cereal Mills, Paris, Ill.

[21] Appl. No.: 36,750

[22] Filed: May 7, 1979

[51] Int. Cl.$^2$ ................................................ C08L 1/02
[52] U.S. Cl. .......................... 260/17.4 GC; 128/284; 128/285; 128/290 R; 128/296; 47/DIG. 10
[58] Field of Search ................................ 260/17.4 GC

[56] References Cited

U.S. PATENT DOCUMENTS

| | | | |
|---|---|---|---|
| 4,028,290 | 6/1977 | Reid | 260/17.4 GC |
| 4,036,588 | 7/1977 | William et al. | 260/17.4 GC |
| 4,045,387 | 8/1977 | Fanta et al. | 260/17.4 GC |
| 4,051,086 | 9/1977 | Reid | 260/17.4 GC |

*Primary Examiner*—Edward M. Woodberry
*Attorney, Agent, or Firm*—Burns, Doane, Swecker & Mathis

[57] ABSTRACT

Absorbent polymeric compositions are disclosed which are prepared by graft copolymerizing acrylonitrile onto an amylaceous material—formaldehyde substrate and then subjecting the graft copolymer to alkaline saponification. The resulting absorbent polymeric composition sets up into a hard gel after absorbing multiple weights (e.g., up to about 3,000 times its own weight) of water.

12 Claims, No Drawings

ABSORBENT POLYMERIC COMPOSITIONS DERIVED FROM AMYLACEOUS MATERIAL-FORMALDEHYDE SUBSTRATES

BACKGROUND OF THE INVENTION

Processes for polymerizing acrylonitrile with starch are well known in the art. For example, such processes are shown in U.S. Pat. Nos. 2,922,768; 3,201,336; 3,661,815; 3,669,915; 3,935,099; 3,985,616; 3,997,484; 4,005,040; 4,045,387; and 4,069,177.

Most of these processes make use of amylaceous (i.e., starch-containing) materials such as pearl starch to produce a graft copolymer which forms a highly water absorbent polymeric composition. These starch-containing polymers can absorb water in amounts of 1,000 times or more by weight of water per weight of the polymeric composition. These products are highly useful in many applications including such uses as incorporation in disposable diapers, surgical pads and sheets, paper towels, disposable paper pads and the like.

The above-mentioned U.S. Pat. No. 4,045,387 discloses a process for producing a highly absorbent polymeric composition which is derived from flour such as corn or wheat flour. While the process disclosed therein is purported to produce a product which will absorb from 1,800 to 3,000 times its weight of deionized water, it has been found that when corn flour is used in the process of this patent to produce a polymeric composition, said composition forms a soft gel. That is, the polymeric composition becomes a highly fluid-like gel material as it absorbs the water.

Polymeric compositions formed from pearl starch, however, using some of the known processes form what is known as a hard gel i.e., a gel which assumes a three-dimensional form and exhibits some rigidity. The formation of the hard gel has a number of advantages in certain applications, such as, for example in seed coating and in disposable diapers as well as in other areas. However, it has been found impossible to produce the hard gel from corn flour utilizing the process of the aforesaid U.S. Pat. No. 4,045,387.

Such a process would be advantageous since corn flour is relatively inexpensive in comparison to pearl starch and is readily available without extensive processing of the corn.

OBJECTS AND SUMMARY OF THE INVENTION

It is an object of this invention to provide a process for forming a polymeric composition which will absorb large amounts of water in a hard gel form.

It is also an object of this invention to provide a process for the formation of the polymeric composition from amylaceous materials such as corn flour which will absorb large amounts of water in the hard gel form.

It is further an object of this invention to provide a polymeric composition which will absorb large amounts of water in the hard gel form.

It is still further an object of this invention to obviate or substantially eliminate the disadvantages of the prior art as outlined above.

In one aspect of the present invention there is provided a process for forming a water-insoluble, aqueous fluid-absorbing graft copolymer comprising: (a) mixing an amylaceous material with a formaldehyde solution containing from about 0.5 to about 9 weight percent of formaldehyde based on the weight of the material to form an amylaceous material-formaldehyde substrate; (b) graft copolymerizing acrylonitrile onto the amylaceous material-formaldehyde substrate to form a graft copolymer; (c) saponifying the graft copolymer in an aqueous solution to form a watersoluble saponified graft copolymmer; and (d) isolating and drying said saponified graft copolymer to form a waterinsoluble, aqueous fluid-absorbing copolymer.

In another aspect of the present invention there is provided an aqueous fluid-absorbing composition comprising a water-insoluble, alkali salt of a saponified graft copolymer of acrylonitrile and an amylaceous material-formaldehyde substrate, said graft copolymer being a water-insoluble solid capable of absorbing up to about 3,000 parts by weight of water per part of said water-insoluble solid while remaining substantially as a solid or hard gel.

DETAILED DESCRIPTION OF THE INVENTION

It has been found that the incorporation of a small amount of formaldehyde in solution with an amylaceous material (e.g., corn flour) prior to gelatinization and processing to form a graft copolymer results in the ultimate formation of a water-insoluble, aqueous fluid-absorbing polymeric composition which sets up as a hard gel and absorbs up to about 3,000 parts by weight of water per part of the copolymer.

As noted above, corn flour processed according to a known process, that is, the process of U.S. Pat. No. 4,045,387, produces only a soft gel. The mechanism by which the formaldehyde makes these fundamental changes in the property of the polymer (i.e., the formation of a hard gel) is not fully understood.

In addition, it has been found that the specific action which results from the use of formaldehyde is specific as to formaldehyde. For example, the use of other aldehydes such as acetaldehyde and propionaldehyde does not provide the same type of product, that is, a highly absorbent polymeric composition which sets up as a hard gel. Indeed, the addition of propionaldehyde has been found to render the entire polymerized mass black and unsuitable for any purpose.

An amylaceous material such as corn flour is mixed with formaldehyde in an aqueous solution with the amount of formaldehyde therein being from about 0.5 to about 9, preferably from about 2 to about 4, and most preferably 2.0, weight percent based on the weight of the amylaceous material. If insufficient formaldehyde is employed, a soft gel will be obtained. The aqueous solution may contain formaldehyde in amounts greater than about 9 weight percent in order to produce a hard gel. However, the absorptive capacity of the gel drops significantly when weight percentages of formaldehyde in excess of about 9 weight percent are employed.

It is not clear to what degree the amylaceous material absorbs the formaldehyde in the solution; i.e., the formaldehyde content of the absorbent polymeric compositions of this invention is not known. However, it is known that the admixture of the amylaceous material with a formaldehyde solution containing greater than about 9 percent by weight of formaldehyde based on the weight of the amylaceous material results in a product having a decreased absorptive capacity.

The formaldehyde can be conveniently added to the amylaceous material in the form of a formalin solution which is commercially available and generally contains about 37 percent formaldehyde.

The addition of formaldehyde to starch for other purposes (e.g., inhibiting bacteria formation, for forming thickening polymers) is known as shown in U.S. Pat. Nos. 602,697; 2,407,071; 2,486,399; and 2,838,465. In addition, the use of formaldehyde in processes for modifying cellulose fibers is also quite well known as shown in U.S. Pat. Nos. 3,838,077 and 3,841,832.

The amylaceous material which may be used in the present invention may consist of many types of starch-containing materials which may be either in a crude (i.e., raw) form or in a pure form. In the crude or raw form the material consists predominately of starch but may also contain substantial amounts of moisture, protein, ash, fiber, etc. In its pure state the amylaceous material consists almost exclusively of starch, with few impurities being present.

The amylaceous material may include starchy materials derived from roots and cereal grains. Exemplary rootderived crude starchy materials include tapioca and potato flour. Exemplary cereal grain-derived crude starchy materials include corn flour, wheat flour, and rice flour. Pearl starch is an example of a cereal grain-derived starchy material in its pure form.

Crude materials such as corn flour are the preferred amylaceous material. Corn flour typically contains about 80 percent starch and up to 10 percent protein, with the remainder being made up of fat, fiber, ash, and moisture.

The amylaceous material in dry form is mixed with an aqueous solution of formaldehyde and the mixture is preferably gelatinized. The gelatinization, graft polymerization and saponification steps are performed in accordance with the process of U.S. Pat. No. 4,045,387, the disclosure of which is hereby incorporated by reference.

The amylaceous material-formaldehyde mixture is gelatinized by heating the mixture to an elevated temperature which is typically about 70° C. or higher, i.e., at a temperature of from about 80° to 100° C., in order to obtain a smooth, viscous gelatinized dispersion of the starch contained within the amylaceous material. Gelatinization may be conducted under an inert gas atmosphere, i.e., by bubbling a slow stream of nitrogen through the dispersion.

After gelatinization, the amylaceous materialformaldehyde substrate is cooled and a polyacrylonitrilecontaining starch graft copolymer is then formed by contacting the amylaceous material-formaldehyde substrate with acrylonitrile in the presence of a suitable polymerization catalyst. The mixture is allowed to stand for a suitable period of time, e.g., 2 to 3 hours or more, to form the graft copolymer. Generally, the graft copolymers have a weight ratio of amylaceous material to polyacrylonitrile of from about 3:1 to about 1:3, preferably from about 1.5:1 to about 1:1.5.

The graft copolymer is then saponified with an alkali metal hydroxide, preferably sodium hydroxide or potassium hydroxide. Again, saponification may be performed in accordance with the teachings of U.S. Pat. No. 4,045,387. Generally, however, the graft copolymer is saponified with an alkali metal hydroxide in amounts such that the molar ratio of alkali metal hydroxide to the acrylonitrile repeating unit of the graft copolymer is from about 0.1:1 to about 7:1.

After saponification, which forms the watersoluble form of the polymerized composition, the polymer is isolated and purified by a suitable process such as dialysis, alcohol precipitation, or the like and then dried.

While the particle size of the final product may vary, it has been found that the finer the particle size of the resulting composition, the greater the water absorbency of the polymer. The use of a fine particle size also increases the ease with which the polymer takes up water. Thus, in most applications, relatively finely ground powder will be desired although the ultimate particle size may be selected within a wide range according to the desires of the ultimate user. The choice of particular particle size is well within the skill of the artisan.

The product which is produced by the present invention has a water absorbency of greater than 1,000 parts of water per part of the copolymer composition based on the weight of each, and generally in the range of 1,500 to about 3,000 parts of water per part of the composition. The absorbency is measured by adding 100 milligrams of the polymer to a graduate, adding 1000 milliliters of water, stirring the mixture and allowing it to stand for 4 hours. The absorbency of the gel is determined by noting the milliliter mark on the graduate which corresponds to the top of the resulting hydrated gel and then multiplying by a factor of ten. For example, if the top of the gel layer is found to correspond to the 180 milliliter graduation, the absorbency of the gel is 1800 milliliters of water per gram of dry polymer, or a ratio of 1800:1. A piece of tissue paper can be dropped into the graduate to help locate the gelwater boundary. It will settle through the water until it contacts the top surface of the gel where it will stop.

The product is further characterized in that the polymer, when in the water-absorbent state, is in the form of a hard gel, i.e., a gel which assumes a three-dimensional form as it sets up. The gel also exhibits some rigidity while not being essentially solid.

As a simple illustration of the difference between a hard gel and a soft gel, it has been found that when an amount of the polymer produced from corn flour according to the process of U.S. Pat. No. 4,045,387 and an equal amount of a polymer produced by the process of the present invention are each placed in separate beakers with the same amount of water, e.g., 200 parts of water per part of polymer, the polymer produced according to the process of U.S. Pat. No. 4,045,387 absorbs the water and becomes a soft gel (i.e., a fluid gel) which runs out of the beaker when the beaker is turned upside down. Only a very few discrete particles of the polymer composition can be observed therein. In contrast thereto, the polymer of the present invention absorbs the water and forms a clear transparent hard gel which remains in place when the beaker is turned upside down. The gel can be removed from the beaker only by applying a force thereto. The gel of the present invention does not retain the shape of the beaker upon removal but becomes gravitationally deformed (i.e., sags or spreads out somewhat), although a three-dimensional form is retained. It can be observed that the body of the gel is composed entirely of discrete particles of the polymer.

The present invention is additionally illustrated in connection with the following Examples, which are to be considered illustrative of the present invention but should not be considered limiting thereto.

EXAMPLE I

A 1000 milliliter flask is charged with 25 grams of yellow corn flour and 420 milliliters of distilled water.

Then 1.5 milliliters of 37 percent formalin are added and mixed into the slurry. The mixture is stirred slowly and heated for 15 minutes at 180° F. to gelatinize the starch in the flour. The dispersion is then cooled to 100° F. and 38 grams of acrylonitrile are added and mixed into the dispersion. A solution of 0.85 grams of ceric ammonium nitrate dissolved in 7 milliliters of 1N nitric acid are then added. The mixture is held under nitrogen for 2 hours and brought to a pH of 7 with a solution of sodium hydroxide. An additional 300 milliliters of distilled water are then mixed into the mixture, and the mixture heated to a temperature of 180° F. and held at that temperature for 15 minutes to drive off excess acrylonitrile. Then 26 grams of sodium hydroxide dissolved in 50 milliliters of water are mixed into the graft slurry and the temperature raised to 190° F. The slurry is stirred intermittently until it becomes viscous enough to prevent settling. The temperature is maintained at 190° F. for the duration of the saponification step. A light yellow color is obtained after about 2 hours, indicating that the saponification step is completed.

After saponification, the pH of the slurry is adjusted to between 6.5 and 7.5 by adding acetic acid. The copolymer is then isolated by rapidly adding one liter of absolute methanol to the saponified material under agitation. An additional alcohol wash is then conducted using one liter of methanol. The alcohol is then removed and the copolymer is dried at a temperature of 150° F. in a hot air oven.

EXAMPLE II

A 100 milliliter flask is charged with 25 grams of rice flour (prepared by grinding polished rice) and 420 milliliters of distilled water. Then 1.5 milliliters of 37 percent formalin are added and mixed into the slurry. The slurry is then stirred slowly and heated for 15 minutes at 180° F. to gelatinize the starch contained in the rice flour. The dispersion is then cooled to 100° F. and 38 grams of acrylonitrile are added and thoroughly mixed into the dispersion. A solution of 1.25 grams of ceric ammonium nitrate dissolved in 7 milliliters of 1 N nitric acid is then added and mixed into the dispersion. The mixture is held under a nitrogen blanket for 2 hours. The pH of the mixture is adjusted to 7 with a sodium hydroxide solution. An additional 100 milliliters of distilled water are then mixed into the mixture, and the mixture is heated to a temperature of 180° F. and held for 15 minutes to boil off excess acrylonitrile. Then 25 grams of sodium hydroxide dissolved in 50 milliliters of water are mixed into the graft slurry and the temperature raised to 190° F. The slurry is then stirred intermittently until it becomes viscous enough to prevent settling. The temperature is maintained at 190° F. for the duration of the saponification. A light yellow color is obtained after approximately 2 hours, indicating that saponification is complete.

After saponification, the pH is adjusted to 7 with acetic acid. The copolymer is then isolated and purified by the rapid addition of 1 liter of absolute methanol to the saponified material under agitation. An additional alcohol wash is conducted using 1 liter of absolute methanol. The alcohol is then removed and the copolymer is dried at 150° F. in a forced air oven.

One hundred milligrams of the polymer are placed in a 1000 milliliter graduate together with 1000 milliliters of water and the gel is allowed to hydrate. After 4 hours, the amount of water absorbed is determined by observing the top level of the gel layer within the graduate. The absorbency of the polymer is 3000 milliliters per gram.

Eighty milliliters of distilled water are then added to 400 milligrams of the dried polymer for a 200:1 dilution. After several minutes, the container could be inverted without the gel falling therefrom.

EXAMPLE III

A potato is peeled and a section analyzed for moisture content. Slices of the potato equivalent to 25 grams of dry solids are then placed into a Waring blender with 400 milliliters of distilled water. The slices are then blended to a pulpy consistency. The mixture is then filtered through a Whatman No. 4 filter paper and reslurried with 420 milliliters of distilled water. Then 1.5 milliliters of 37 percent formalin are added and the slurry is mixed. The slurry is then heated to 180° F. and held at that temperature for 15 minutes to gelatinize the starch contained in the potato slurry. The dispersion is then cooled to 100° F. and 38 grams of acrylonitrile are added and mixed into the dispersion. A solution of 1.25 grams of ceric ammonium nitrate dissolved in 7 milliliters of 1N nitric acid is then added to the dispersion. The mixture is held under a nitrogen blanket for 2 hours to allow graft polymerization to occur. The pH of the mixture is then adjusted to 7.0 with a solution of potassium hydroxide. An additional 100 milliliters of distilled water are mixed into the graft mixture and the mixture heated to a temperature of 180° F. and held for 20 minutes to boil off any excess acrylonitrile that might be present. Then 42 grams of potassium hydroxide, dissolved in 50 milliliters of water, are mixed into the graft mixture and the temperature further increased to 190° F. The slurry is stirred intermittently until it becomes viscous enough to preclude settling. The temperature is maintained at 190° F. for the duration of the saponification step. A light yellow color is obtained after approximately 2 hours, indicating that saponification was complete.

The pH is then adjusted to 7.0 with acetic acid and the polymer isolated and purified in the same manner as previously described in Examples I and II.

The water absorbency determined by means of the graduate test ( i.e., 100 milligrams of polymer in 1000 milliliters of distilled water) is 1700:1.

A 200:1 dilution of the polymer does not flow from an inverted container.

COMPARATIVE EXAMPLE A

The process of Example I is repeated with corn flour except that distilled water alone is utilized instead of the formalin-containing solution in the original mixture-forming step. The polymer is then made in exactly the same manner. Upon testing to determine water absorbency, it is found that the polymer absorbed 3500 milliliters of water. When a 200:1 dilution of the polymer is prepared as described above, the resultant gel flows easily from the inverted container. The differences in physical properties between the hard corn flour gel of Example I and the soft corn flour gel of this Comparative Example can best be seen from the following tests:

(a) Brookfield viscosity method

A Brookfield Model LVF viscometer was used to measure the viscosity of the gels prepared with and without formaldehyde as well as a gel prepared from pearl starch without formaldehyde. For most concentrations, a number 4 spindle was used at speeds of 6 or 12 rpm. At the lowest concentrations of gels or at the lower viscosities a number 3 spindle was used with the above speeds.

Initially, 6 grams of a dry polymer are placed into 600 milliliters of distilled water and allowed to hydrate for 16 hours. This results in a 100:1 dilution of the polymer. After hydration is completed, the viscosity of the gel is measured using the viscometer. The more fluid the material is, the lower its viscosity will be. Greater dilutions of the polymer are made by adding additional distilled water. The gel is allowed to stand 30 minutes before measuring the viscosity. The results of this testing are tabulated below:

Table I

| Gels | Brookfield Viscosities (centipoise) Dilutions | | | |
|---|---|---|---|---|
|  | 100:1 | 200:1 | 400:1 | 800:1 |
| Corn flour gel without formaldehyde | 5,500 cps | 2,500 cps | 1,400 cps | 825 cps |
| Corn flour gel with formaldehyde | 85,000 cps | 84,000 cps | 72,000 cps | 7,000 cps |

(b) Bostwick consistometer method

The Bostwick consistometer is a device used throughout the food industry for measuring the consistency and/or flowability of various materials.

The gels, hydrated and diluted in the manner described in (a) above, are tested by first placing the gel in a reservoir of standard size, then rapidly raising one side of the reservoir and allowing the gel to flow along a calibrated channel. The channel is scaled in centimeters. The more fluid the material is, the greater the number of centimeters that it will flow. The Bostwick apparatus has a range of 0–24 centimeters. Readings are taken 15 seconds after opening the reservoir.

A reading of zero centimeters in 15 seconds would therefore represent a substance which does not flow and behaves as a solid, while a maximum reading of 24 centimeters would represent a flowable material which behaves as a liquid.

The results of the testing are tabulated below:

Table II

| Sample Gels | Bostwick Readings (cm.) at Given Dilutions Dilutions | | | |
|---|---|---|---|---|
|  | 100:1 | 200:1 | 400:1 | 800:1 |
| Corn flour gel without formaldehyde | 11.0 | 16.5 | 21.0 | 22.5 |
| Corn flour gel with formaldehyde | 0.25 | 1.0 | 3.0 | 11.75 |

(c) Dropping ball viscosity method

For this test the gels are hydrated and diluted as before. They are then placed in glass cylinders to give a column depth of gel of 33 centimeters in height. The cylinder diameter is 4.7 centimeters. A lead ball of 1.128 centimeters in diameter and weighing 8.473 grams is then released at the top surface of the gel column and timed until it reaches the bottom of the gel column. The thicker or more solid the gel, the longer it takes the ball to reach the bottom of the gel column. Conversely, the more fluid the gel, the faster the ball reaches the bottom of the gel column. The test results are tabulated below:

Table III

| Sample Gels | Dropping Ball Time (Seconds) at Given Dilutions Dilutions | | | |
|---|---|---|---|---|
|  | 100:1 | 200:1 | 400:1 | 800:1 |
| Corn flour gel without formaldehyde | 1.1 | 0.4 | 0.1 | 0.1 |
| Corn flour gel with formaldehyde | 1000 | 1000 | 116.0 | 0.5 |

COMPARATIVE EXAMPLE B

The process of Example II is repeated with rice flour except that distilled water alone is utilized instead of the formalin-containing solution in the original mixture-forming step. The polymer is then made in exactly the same manner. Upon testing for water absorbency, the polymer was found to absorb 4000 milliliters of water per gram. When a 200:1 dilution of the polymer is prepared as before, the hydrated gel flows easily from the inverted container.

Dilutions of the rice flour gels prepared with and without formaldehyde are tested by the dropping ball method.

The results are tabulated below:

Table IV

| Sample Gels | Dropping Ball Time (Seconds) At Given Dilutions Dilutions | | |
|---|---|---|---|
|  | 200:1 | 400:1 | 800:1 |
| Rice flour gel without formaldehyde | 0.6 | 0.4 | 0.2 |
| Rice flour gel with formaldehyde | 1000 | 317 | 37.0 |

COMPARATIVE EXAMPLE C

A process similar in procedure to Example III is conducted with crude potato starch by treating a potato as previously described but utilizing only distilled water in the initial mixing step. The polymer is then prepared, isolated and purified in the same manner as before.

Upon testing for water absorbency, the polymer is found to absorb water in a ratio of 3000:1. A 200:1 dilution of the polymer easily flows from an inverted container unlike the polymer produced in Example III.

Dilutions of the crude potato starch polymer prepared with and without formaldehyde are tested by the dropping ball method. The results are tabulated below:

TABLE V

| Sample Gels | Dropping Ball Time (Seconds) at Given Dilutions Dilutions | | |
|---|---|---|---|
|  | 100:1 | 200:1 | 400:1 |
| Crude potato starch gel without formaldehyde | 20.8 | 6.2 | 2.0 |
| Crude potato starch gel with formaldehyde | 1000 | 1000 | 69.2 |

COMPARATIVE EXAMPLE D

The procedure of Example I is also followed using propionaldehyde in place of formaldehyde. The product which is formed is black in color and is totally unsuitable for use as a water-absorbent material.

While the invention has been described in connection with a preferred embodiment thereof, it is to be understood that the present disclosure is illustrative rather than restrictive and further modifications may be resorted to without departing from the spirit of the invention or the scope of the claims.

We claim:

1. A method of forming a water-insoluble, aqueous fluid-absorbing copolymer comprising:
   (a) mixing an ungelatinized amylaceous material with a formaldehyde solution containing from about 0.5 to about 9 weight percent formaldehyde based on the weight of the amylaceous material to form an amylaceous material-formaldehyde substrate;
   (b) graft copolymerizing acrylonitrile onto the amylaceous material-formaldehyde substrate to form a graft copolymer;
   (c) saponifying the graft copolymer in an aqueous solution to form a water-soluble saponified graft copolymer; and
   (d) isolating and drying said saponified graft copolymer to form a water-insoluble, aqueous fluid-absorbing copolymer.

2. The method of claim 1 wherein said mixture of amylaceous material and formaldehyde solution is gelatinized prior to step (b).

3. The method of claim 1 wherein said formaldehyde-containing solution contains from about 2 to about 4 weight percent formaldehyde based on the weight of the amylaceous material.

4. The method of claim 1 wherein the weight ratio of said substrate to acrylonitrile in the graft copolymer is from about 3:1 to about 1:3.

5. The method of claim 1 wherein the graft copolymer is saponified with an alkali metal hydroxide in amounts such that the molar ratio of alkali metal hydroxide to the acrylonitrile repeating unit of the graft copolymer is from about 0.1:1 to about 7:1.

6. The method of claim 1 wherein the amylaceous material is selected from the group consisting of root and cereal grain-derived starch-containing materials.

7. The method of claim 6 wherein the amylaceous material is corn flour.

8. The product of the process of claim 1.

9. An aqueous fluid-absorbing composition comprising a water-insoluble alkali salt of saponified graft copolymers of acrylonitrile and an amylaceous material-formaldehyde substrate, said graft copolymer being a water-insoluble solid capable of absorbing up to about 3000 parts by weight of water per part of said water-insoluble solid while remaining substantially as a solid gel.

10. The composition of claim 9 wherein the amylaceous material is selected from the group consisting of root and cereal grain-derived starch-containing materials.

11. The composition of claim 10 wherein the amylaceous material is corn flour.

12. The composition of claim 9 wherein said amylaceous material-formaldehyde substrate is formed by mixing an ungelatinized amylaceous material with a formaldehyde solution containing from about 0.5 to about 9 weight percent formaldehyde based on the weight of amylaceous material.

* * * * *